United States Patent [19]

Jewusiak

[11] 4,424,810
[45] Jan. 10, 1984

[54] PLASTIC LIGATING CLIPS

[75] Inventor: Stephen J. Jewusiak, Denville, N.J.

[73] Assignee: Ethicon, Inc., Somerville, N.J.

[21] Appl. No.: 244,436

[22] Filed: Mar. 16, 1981

[51] Int. Cl.³ .............................................. A61B 17/12
[52] U.S. Cl. .................................... 128/326; 128/346; 128/321
[58] Field of Search ............... 128/322, 325, 346, 326, 128/321

[56] References Cited

U.S. PATENT DOCUMENTS

| 3,032,039 | 5/1963 | Beaty | 128/346 |
| 3,247,852 | 4/1966 | Schneider | 128/325 |
| 3,270,745 | 9/1966 | Wood | 128/325 |
| 3,378,010 | 4/1968 | Codling et al. | 227/DIG. 1 |
| 3,616,497 | 11/1971 | Esposito, Jr. | 128/346 |
| 3,705,586 | 12/1972 | Sarracino | 128/346 |
| 3,713,622 | 1/1973 | Dinger | 128/346 |
| 3,825,012 | 7/1974 | Nicoll | 128/346 |
| 3,874,042 | 4/1975 | Eddleman et al. | 128/346 |
| 3,926,195 | 12/1975 | Bleier et al. | 128/346 |
| 4,345,600 | 8/1982 | Rothfuss | 128/346 |

Primary Examiner—C. W. Shedd
Attorney, Agent, or Firm—Robert L. Minier

[57] ABSTRACT

Plastic ligating clips of absorbable or nonabsorbable materials are formed by two legs joined with a resilient hinge. One leg terminates in a hook member which secures the other leg when the clip is closed. Each leg of the clip is provided with an indentation extending across its width near the distal end which secures the clip in the applier and allows the clip to rotate about its hinge during closure. The clip applier is a forceps-type instrument having channeled jaws especially adapted to receive and close the plastic clip.

10 Claims, 6 Drawing Figures

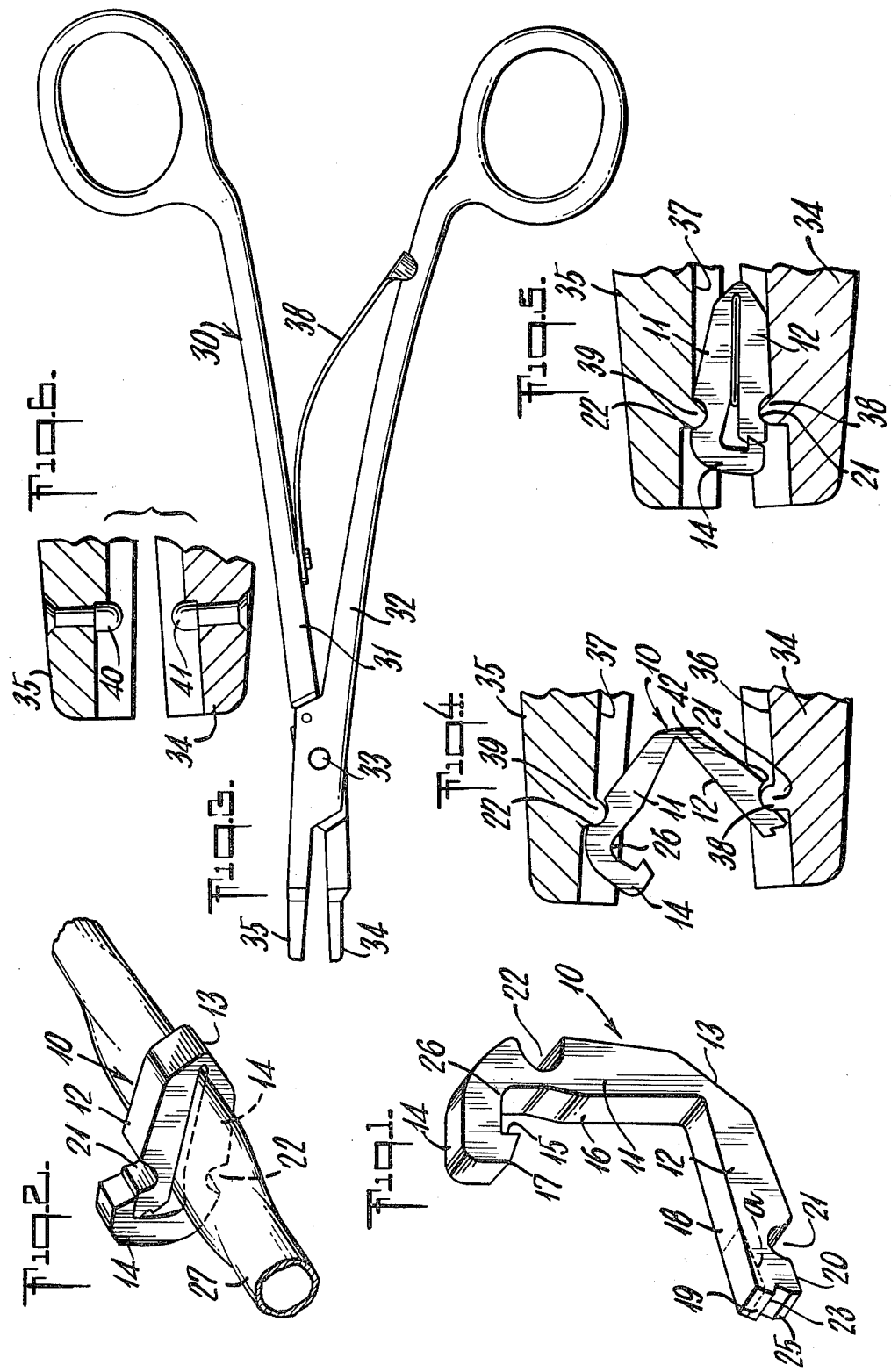

PLASTIC LIGATING CLIPS

BACKGROUND OF THE INVENTION

The present invention relates to hemostatic clips and clip appliers, and, more particularly, to hemostatic clips fabricated from absorbable or nonabsorbable polymeric materials and to instruments for applying such clips to blood vessels and the like.

Hemostatic clips are utilized in surgical procedures to close severed blood vessels and other small fluid ducts. In the past, hemostatic clips have been narrow U-shaped or V-shaped strips formed of tantalum or stainless steel which are capable of being deformed and possess sufficient strength to retain the deformation when clamped about a blood vessel. The clips are generally applied using a forceps-type device having jaws channeled or otherwise adapted to hole the open clip. Representative hemostatic clips and appliers of the prior art are best illustrated in U.S. Pat. Nos. 3,867,944; 3,631,707; 3,439,523; 3,439,522; 3,363,628; 3,312,216; and 3,270,745.

It has been suggested in the prior art, as in U.S. Pat. No. 3,439,523, for example, that hemostatic clips might be formed of inexpensive plastics or materials which are slowly absorbable in the body. Unfortunately, conventional U- and V-shaped hemostatic clips do not posses the required strength or deformability when constructed of known plastic materials to be successfully clamped about a blood vessel. Thus, although the need and desirability of providing inexpensive plastic ligating clips of both absorbable and nonabsorbable materials has been recognized for over ten years, there has been no practical way to satisfy this need.

U.S. Pat. No. 3,926,195 describes a small, plastic clip designed for the temporary or permanent close of the oviduct and vas deferens in humans. These clips preferably have a clamping surface of from 6 to 10 mm in length and 3 to 6 mm in width. The size of such clips are accordingly considerably larger than is desirable for hemostatic clips. Additionally, clips of U.S. Pat. No. 3,926,195 require the use of several complex tools to apply the clips which are acceptable for the purposes described in the reference but would be unacceptable in a surgical procedure requiring the rapid placement of a large number of hemostatic clips to stem the flow of blood from severed vessels.

It is accordingly an object of the present invention to provide a plastic ligating clip effective for clamping off small blood vessels and other fluid ducts in the body. it is a further object of this invention to provide plastic ligating clips of both absorbable and nonabsorbable materials. It is yet a further object of this invention to provide plastic ligating clips which are quickly and easily applied to severed blood vessels and other fluid ducts with a single forceps-type instrument such as those used in applying metallic clips.

SUMMARY

The ligating clips of the present invention comprise two legs joined at the proximal ends thereof along a line forming a resilient hinge, with the first leg terminating in a deflectable hook member adapted to engage the distal end of the second leg. Each leg is provided with an indentation extending across the width of the leg near the distal end thereof. The indentation on the second leg is spaced from the distal end thereof by a distance equal to the depth of the hook member of the first leg. The indentation on the first leg is aligned with the indentation on the second leg so that the major axis along the length of the clip is normal to the minor axis extending through each indentation when the clip is closed and locked.

The applier for the clips of the present invention is a forceps-type instrument wherein each jaw is channeled to receive the width and length of the clip and a flange is provided across the base of each channel to engage the indentation on each leg ot the clip. The depth of the channel in each jaw forward of the flange (between the flange and the tip of the jaw) is greater than to the rear of the flange. When the open clip is placed between the jaws of the applier, it is held firmly in place with the indentation of each leg engaged by the flange of each jaw. As the jaws are closed, the clip is maintained in position in the applier by the engagement of the indentations by the flanges and the distal end of the second leg bypasses and locks under the hook member of the first leg.

The clips may be formed of plastic by injection molding or other suitable technique, and may be composed of a nonabsorbable material such as polypropylene or an absorbable material such as a homopolymer or copolymer of lactide and glycolide. The clips are formed in a normally open position and constructed with a small amount of material to minimize tissue reaction. The clips are readily applied with a forceps-type applier using conventional surgical techniques.

DESCRIPTION OF DRAWINGS

FIG. 1 is a greatly enlarged view in perspective of a surgical clip according to the present invention.

FIG. 2 illustrates the clip of FIG. 1 clamped about a blood vessel.

FIG. 3 illustrates a forceps-type applier useful with the clips of the present invention.

FIG. 4 illustrates the open clip of FIG. 1 retained in the jaws of a forceps-type clip applier.

FIG. 5 illustrates the clip of FIG. 4 closed and locked over a blood vessel in the jaws of the applier.

FIG. 6 illustrates an alternate construction of the jaws of the forceps-type clip applier.

DESCRIPTION OF PREFERRED EMBODIMENTS

Referring now to FIG. 1, there is illustrated hemostatic clip 10 constructed of two leg segments 11 and 12 connected at the proximal ends thereof by hinge section 13. Leg 11 terminates at the distal end thereof in hook member 14 having inner face 15 substantially parallel to inner face 16 of leg 11 and forming an acute angle with end face 17. Leg member 12 terminates at the distal end in end face 19 which forms an obtuse angle with inner face 18 of leg 12. End face 19 is offset at 23 to form a notch approximately midway between surfaces 18 and 20, and additionally is squared off at face 25 to form a substantially right angle with surface 20.

The length and width of faces 16 and 18 are substantially equal, and face 15 of hook 14 is spaced from face 16 of leg 11 by a distance corresponding to the thickness of leg 12 between the plane of face 18 and surface 20. When legs 11 and 12 are pivoted about hinge 13 to bring faces 18 and 16 into opposition, hook 14 is deflected by surface 19 of leg 12 until the distal end of leg 12 snaps under hook 14 and is thereby locked in place. End face 17 of hook 14 and end face 19 of leg 12 are angled as illustrated to facilitate the passage of leg 12 past hook 14 during clip closure.

When the clip is closed over a tubular vessel as illustrated in FIG. 2, surfaces 16 and 18 engage and compress vessel 27 to close the lumen thereof. Surfaces 16 and 18 may be smooth as illustrated in FIG. 1, or may be provided with ridges or grooves to increase vessel holding power. Leg 11 may also be undercut at the juncture of hook member 14 and surface 16 as illustrated at 26 in FIG. 1 to increase the deflectability of hook member 14 and increase the space between the hook member 14 and leg 11, thereby compensating for any inward deflection of hook 14 during closure which might reduce the clearance between surfaces 15 and 16 and otherwise interfere with the latching of the clip.

Referring again to FIG. 1, leg 12 of clip 10 includes an indentation 21 extending across the width of the leg near the distal end thereof. Indentation 21 is spaced from surface 25 a distance sufficient to permit full engagement of hook member 14 by leg 12 when the clip is in a closed position using an applier having a flange which engages the indentations of the clip. Indentations 21 and 22 are equidistant from hinge means 13 so that when the clip is closed, indentations 21 and 22 define a line perpendicular to the major axis along the length of the clip as best illustrated in FIG. 5.

The distal end of leg 12 forward indentation 21 is of reduced thickness relative to the thickness immediately to the rear of indentation 21, thereby forming step 24 between indentations 21 and surface 20. The significance of this clip configuration will be appreciated in connection with the instrument used to apply and close the clip as illustrated in FIGS. 3 through 5.

FIG. 3 illustrates a forceps-type ligating clip applier 30 comprising two handle members 31 and 32 crossing at hinge point 33 and maintained in a normally open position by spring 38. Handle 31 extends beyond hinge 33 forming jaw member 34 while the extension of handle 32 forms jaw member 35.

FIG. 4 illustrates the detail of the construction of jaws 34 and 35 and the interaction of the jaws with the clip of FIG. 1. Jaws 34 and 35 are of identical design and are provided respectively with channels 36 and 37 extending rearwardly from the tips of the jaws. Each channel is provided with a flange 38 and 39 respectively across the width of the channel and near the distal end thereof. Flanges 38 and 39 are in alignment when the jaws of the applier are closed and are sized to engage the indentations 21 and 22 of the clip. Channels 36 and 37 forward of flanges 38 and 39 are deeper than to the rear of the flanges as illustrated in FIG. 4. When the open clip is held in the applier, the indentations on the clip are engaged by the flanges in each jaw. Due to the angle of the clip in the applier, the distal ends of legs 11 and 12 extend into the deeper forward channel section of each jaw. The reduced thickness of leg 12 at the distal tip prevents interference between the tip and the channel of the applier when the clip is held in the open position as illustrated in FIG. 4. Also, the raised shoulder 42 facilitates the lifting or pulling of the clip as from a cartridge or similar clip receptacle when loading the applier.

Clip 10 is initially loaded in applier 30 in the open position as illustrated in FIG. 4. After moving the jaws of the applier and the clip into position over the vessel to be ligated, the jaws of the applier are closed and the clip is locked in position over the vessel as illustrated in FIG. 5. As the clip is closed, the indentations of legs 11 and 12 are engaged by flanges of jaws 37 and 36 and maintained in position in the applier until the outer surface of leg 12 rests on the base of channel 36 as illustrated in FIG. 5. At this point, the distal end of leg 12 has rotated away from the base of the channel and sufficient space exists for hook 14 to bypass leg 12 and latch over the outer surface thereof. After the clip has been securely latched over the vessel to be ligated, the jaws of the applier are opened to release the clip and vessel and a new clip is loaded in the applier. Since the jaws of the applier are identical, it is not necessary to orient the applier to the clip when loading the applier.

FIG. 5 illustrates an alternative construction of the jaws of the applier, wherein the flange or projection in the channel of the applier is constructed by fixing a rivet 40 in a hole 41 disposed in the channel of each jaw of the applier. The hole may extend into the jaw of the applier or may extend entirely therethrough.

Many variations in the clip design other than the embodiments disclosed herein will be apparent to those skilled in the art and are contemplated within the scope of the present invention. For example, the undercut at the juncture of hook 14 and surface 16 of leg 11 may be omitted, and the inner surface of leg 12 may be beveled at the distal end as indicated by broken line a in FIG. 1 to compensate for downward deflection of hook 14 during closure which might reduce the clearance under face 15 and interfere with the latching of leg 12. Offset 23 in end face 19 of leg 12 provides an intermediate latching position and effectively increases the length of face 18 at the distal end of leg 12, but may be omitted if desired. These and other modifications in the configuration of the clip may be employed without departing from the spirit and scope of the present invention.

The clips of the present invention may be constructed in various sizes according to their intended function. Hemostatic clips are typically less than 6 mm in length, about 1.5 mm in width, and have a vessel clamping surface about 3 mm in length. The dimensions of the clip may be reduced by about 50 percent for certain applications in microsurgery. Larger clips for special hemostatic applications and other functions such as closure of oviducts or vas deferens may have dimensions of about double those of a typical hemostatic clip. The various sizes of clips are preferably matched with individual appliers having jaws tailored to the size of the clip for best performance.

The clips of the present invention are most conveniently molded of biologically acceptable plastic materials which may be absorbable or nonabsorbable. Preferred absorbable polymers include homopolymers and copolymers of glycolide and lactide, and poly(p-dioxanone). Preferred nonabsorable polymers include nylon and polypropylene. All these materials have been demonstrated to be biologically acceptable when used as sutures or other implantable medical devices. The clips may also be cast or machined from solid polymeric materials or from metals such as aluminum, magnesium, stainless steel, tantalum, and various alloys of these, some of which may also be absorbable in biological tissue.

What is claimed is:

1. A sterile, hemostatic clip for application using a clip applying instrument, said instrument including means for gripping and manipulating said clip, said clip comprising:

first and second leg members joined at their proximal ends by resilient hinge means and terminating at their distal ends in latch means, each leg member having an outer surface and a vessel clamping inner face in opposition to the vessel clamping inner face of the other leg member;

said first leg member terminating at the distal end thereof in latch means comprising a deflectable hook member extending from the inner face of said leg member, said hook member having an inner face spaced from and substantially parallel to the inner face of said leg member, said leg member including a substantially semi-cylindrical indentation extending across the width of the leg member on the outer surface thereof and spaced from the proximal end thereof;

whereby said first leg member is allowed to move with respect to said instrument means for gripping and manipulating said clip as the clip is being closed;

said second leg member terminating at the distal end thereof in latch means comprising a surface adapted to deflect said hook member and enter said space between the inner face of said hook member and the inner face of said first leg member, said second leg member including a substantially semi-cylindrical indentation extending across the width of the leg member on the outer surface thereof and spaced from the distal and proximal ends thereof, whereby said second leg member is allowed to move with respect to said instrument means for gripping and manipulating said clip as the clip is being closed; said indentation on said second leg member being spaced from the distal end of said leg member by a distance corresponding to the length of the inner face of the hook member;

the indentations of said first and second leg members being spaced equidistantly from said hinge means;

whereby said clip may be applied using a clip applying instrument which instrument grips the clip using the indentations in said leg members and applies the clip to the vessel to be closed by pivoting said first and second leg member about said hinge means to close said clip causing the distal end of said second leg member to deflect and engage the hook member of the first leg member to lock the clip in a closed position.

2. The hemostatic clip of claim 1 wherein the distal end of said second leg member terminates in a surface defining an obtuse angle with the inner face thereof.

3. The hemostatic clip of claim 2 wherein said surface at the distal end of said second leg member is notched.

4. The hemostatic clip of claim 1 wherein said hinge means is defined by a line of minimum clip thickness at the juncture of the inner faces of said first and second leg members.

5. The hemostatic clip of claim 1 wherein said hook member is spaced from the plane of said inner face of said first leg member by a distance equal to at least the thickness of said second leg member distal to said indentation.

6. The hemostatic clip of claim 6 wherein the thickness of the distal end of said second leg member is reduced distal to said indentation.

7. The hemostatic clip of claim 6 wherein said second leg member is beveled at the distal end of said inner face so as to decrease the thickness of said second leg member between said outer surface and said inner face.

8. The hemostatic clip of claim 7 wherein said hook member is spaced from the plane of the inner face of said first leg member by a distance corresponding to at least the unbeveled thickness of the distal end of said second leg member distal to said indentation.

9. The hemostatic clip of claim 1 wherein said first leg member is under-cut at the juncture of said hook member and said inner face of said leg member.

10. The hemostatic clip of claim 1 wherein the surface of said second leg member adapted to deflect said hook member makes an obtuse angle with the vessel clamping inner face of said second leg member.

* * * * *